United States Patent [19]
Christensen et al.

[11] Patent Number: 5,846,745
[45] Date of Patent: Dec. 8, 1998

[54] METHOD AND APPARATUS FOR THE ON-LOCATION FIELD DETECTION OF UNIDENTIFIED ANTIGENIC SUBSTANCES

[75] Inventors: Dale A. Christensen, Orono; Peter Nash, Eden Prairie, both of Minn.

[73] Assignee: Camas Diagnostic Company, Minneapolis, Minn.

[21] Appl. No.: 706,809

[22] Filed: Sep. 3, 1996

Related U.S. Application Data

[63] Continuation-in-part of Ser. No. 402,464, Mar. 10, 1995, Pat. No. 5,552,288, which is a continuation-in-part of Ser. No. 957,686, Oct. 7, 1992, abandoned, which is a division of Ser. No. 555,232, Jul. 20, 1990, Pat. No. 5,156,948.

[51] Int. Cl.$^6$ .................................................. G01N 33/53
[52] U.S. Cl. .............................. 435/7.9; 422/56; 422/57; 422/58; 422/61; 435/7.92; 435/287.1; 435/287.2; 435/287.7; 435/288.1; 435/288.2; 435/288.5; 435/810; 436/169; 436/514; 436/518; 436/524; 436/528; 436/535; 436/805; 436/810; 436/172
[58] Field of Search .................................. 422/55–58, 61; 435/7.9, 7.92, 287.1, 287.2, 287.7, 288.1, 288.2, 288.5, 810; 436/514, 518, 524, 528, 535, 805, 810, 172, 169

[56] References Cited

U.S. PATENT DOCUMENTS

| | | | |
|---|---|---|---|
| 4,275,149 | 6/1981 | Litman et al. | 435/810 |
| 4,299,916 | 11/1981 | Litman et al. | 435/6 |
| 5,156,948 | 10/1992 | Christensen et al. | 435/5 |
| 5,234,840 | 8/1993 | Appleton | 436/518 |
| 5,552,288 | 9/1996 | Christensen et al. | 435/7.9 |

FOREIGN PATENT DOCUMENTS

| | | |
|---|---|---|
| 9204612 | 3/1992 | WIPO . |

*Primary Examiner*—Christopher L. Chin
*Attorney, Agent, or Firm*—Burd, Bartz & Gutenkauf

[57] ABSTRACT

A method and test device are disclosed for detecting under field conditions unidentified antigenic substances which are detrimental to human or animal health or welfare. A sample solution containing the suspected unidentified antigenic substance is added to the test device containing a known antigenic substance which is irreversibly attached to a solid support and suspended in a buffer solution along with an antibody specific to the known antigenic substance conjugated with a detecting agent. After incubation to bind the unknown antigenic substance to the conjugate, the solution contacts a white porous bibulous sheet incorporating a substrate for the detecting agent and a chromogen, which is part of the test device. If the identity of the sample antigen is the same as that on the solid support, a color reaction takes place.

22 Claims, 2 Drawing Sheets

METHOD AND APPARATUS FOR THE ON-LOCATION FIELD DETECTION OF UNIDENTIFIED ANTIGENIC SUBSTANCES

CROSS REFERENCE TO RELATED APPLICATIONS

This application is a continuation-in-part of application Ser. No. 08/402,464 filed Mar. 10, 1995, now U.S. Pat. No. 5,552,288 issued Sep. 3, 1996, which is a continuation-in-part of application Ser. No. 07/957,686 filed Oct. 7, 1992, now abandoned, which in turn is a division of application Ser. No. 07/555,232 filed Jul. 20, 1990, now U.S. Pat. No. 5,156,948 issued Oct. 20, 1992.

BACKGROUND OF THE INVENTION a. Field of the Invention

Many microbial diseases, toxins and chemicals are detrimental to human and animal welfare. Convenient, economical and meaningful test procedures are needed to assist the medical, veterinary, food processing and feed production communities to diagnose and combat these diseases and detrimental effects.

This invention relates to a diagnostic method and test kit which have the advantage of being simple to use, economical, rapid and requiring no special equipment. Since no instruments are required, the test can be run by veterinarians on a farm, by medical and veterinarian personnel in an office setting, in quality control areas of food processing plants, or in other settings where instruments, running water and other laboratory equipment and supplies are not available.

b. The Prior Art

A variety of techniques are available to test for the presence of undesirable agents such as microbes, toxins and harmful chemicals. The test of the present invention falls into the category of antigen detection, as do many other existing tests. Among these are immunodiffusion, enzyme immunoassays, radioimmunoassays, fluorescent immunoassays, chemiluminescent immunoassays, and various chromatographic methods.

The samples for these tests include blood, serum, urine, nasal swabs, extracts of grain or food products, water samples, surface or air samples contained in buffer, and a variety of other liquid samples.

Examples of tests using antibody-enzyme conjugates and solid phase antigen are: Enzyme-Linked Immunosorbent Assays (ELISA), Non-competitive Immunoenzymetric Assays (IEMA), and Competitive Immunometric Assays.

One immunological test system integrates chemical ingredients and physical format or design to allow the proper sequence of chemical and immunological reactions to take place. Another example of a test system possessing these qualities is described in International Patent Publication No. WO 92/04612.

SUMMARY OF THE INVENTION

The present invention relates to tests utilizing a specific antibody to detect an antigen of interest. The antibody is coupled to a detector such as in enzyme-, radio-, fluorescent- and chemiluminesent- immunoassays. The antibody-detector binds with antigen in the sample or becomes bound to antigen attached to a solid matrix. It is pre-prepared and is an embodiment of the test kit.

Broadly defined the invention is a method and test device for detecting unidentified antigenic substances which are detrimental to human or animal health or welfare. In carrying out the method a known antigenic substance, the detection of which is of interest, is irreversibly attached to a solid support, suspended in a buffer solution (solution A), and is placed in the test device. An antibody specific to the known antigenic substance is coupled to a detecting agent to prepare a detecting agent—antibody conjugate solution (solution B). The known antigenic substance on the solid support is contacted by a sample solution (solution C) containing the suspected unidentified antigenic substance to be detected, and the conjugate solution (solution B), and the solutions (solutions A, B and C) are admixed. The mixture is incubated to bind the unknown antigenic substance to the conjugate. A white porous bibulous sheet material incorporating a substrate for the detecting agent and a chromogen, which is part of the test device, is contacted with the conjugate and bound antigen while maintaining the bibulous material separate from the known antigen and support. If the identity of the antigen which is present in the sample is the same as that on the solid support, a color reaction takes place in the bibulous material and can be observed.

The test device comprises a first receptacle of inert transparent or translucent material having a closed end and an open end for receiving the known antigenic substance and solid support, and the sample and conjugate solutions. The first end of a second receptacle having first and second open ends and supporting a transverse liquid permeable barrier is engageable with the open end of the first receptacle. A transparent or translucent closure cap which is engageable with the second open end of the second receptacle includes a white porous bibulous read-out pad in engagement with its inside surface. A chromogen and a substrate for a color reactive detecting agent is incorporated in the pad, which is spaced from the liquid permeable barrier.

BRIEF DESCRIPTION OF THE DRAWINGS

The invention is illustrated by the accompanying drawings in which corresponding parts are identified by the same numerals and in which.

DETAILED DESCRIPTION OF PREFERRED EMBODIMENT

Figures 1, 2:
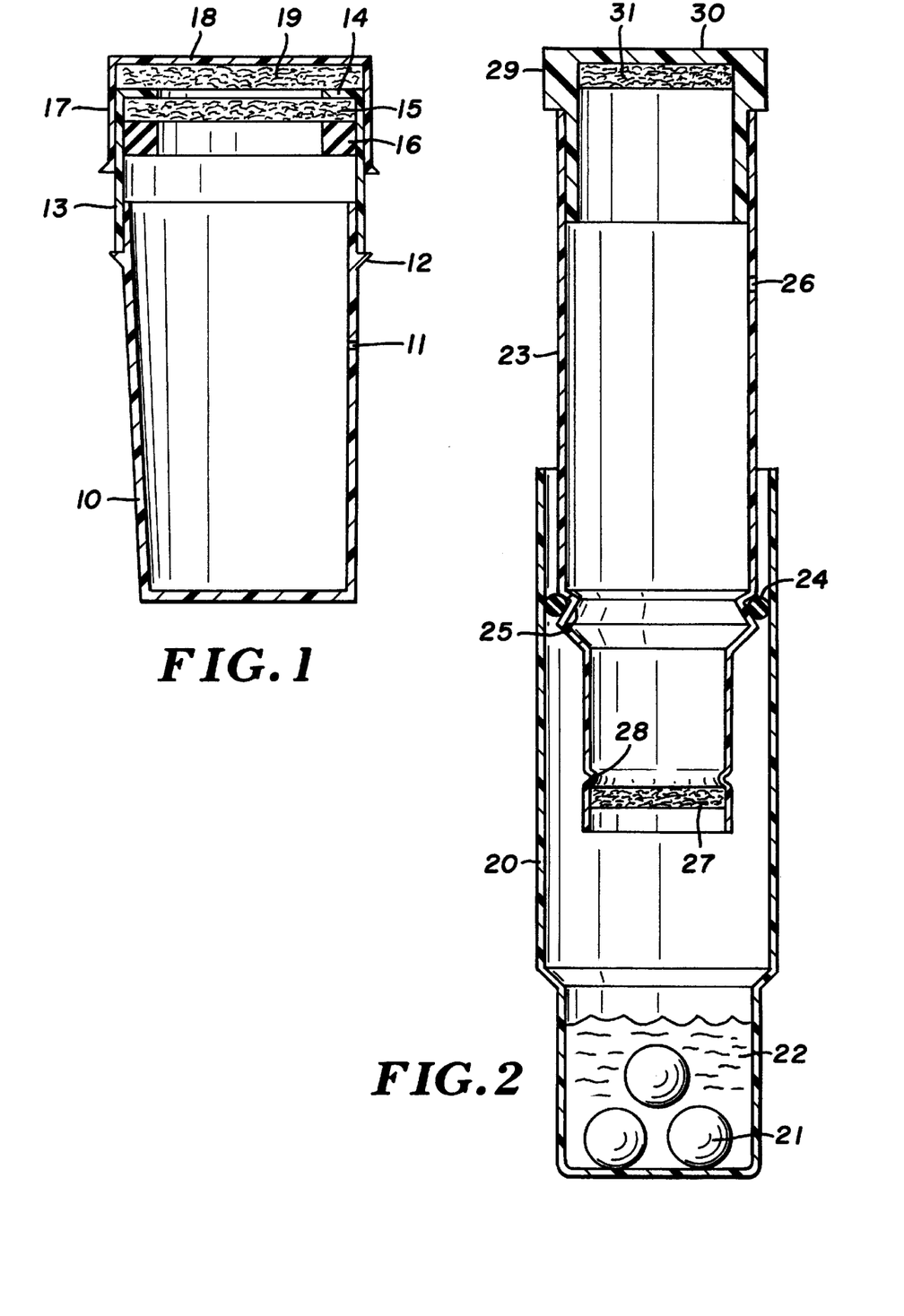
FIG. 1 is a vertical sectional view of one form of detection test device according to the present invention.
FIG. 2 is a vertical sectional view of another form of test device.

Referring to the drawings, and particularly to FIG. 1, there is shown one form of test device including a first receptacle in the form of a cylindrical vial or cup 10, preferably formed from transparent or translucent inert synthetic resinous plastic material, and of a size to receive the test samples and other reactants. A vent 11 is provided in the side wall of cup 10 spaced from the top edge. Vent 11 is provided with a removable closure, such as pressure sensitive adhesive tape.

An outwardly extending flange or lip 12 is provided adjacent the top edge of cup 10.

A second receptacle in the form of a cylindrical collar or sleeve 13 is adapted to fit in leak-proof sealed engagement over the top of cup 10. Lip 12 functions as a stop to limit engagement between the cup and sleeve. Sleeve 12 preferably has an annular inwardly extending lip or flange 14 at its upper end. A liquid permeable barrier 15 in the form of a screen or filter or the like is positioned on the inside of sleeve 12, held in place against flange 14 by a resilient retaining washer 16 press fit into the sleeve.

A transparent or translucent closure cap 17 is adapted to fit in leak-proof sealed engagement with the top of sleeve 13. Cap 17 has a flat top or end 18. A white porous bibulous read-out pad 19 is positioned within cap 17 in contact with the inside surface of end 18. The read-out pad, impregnated with a colorant, may be formed from filter paper, blotting paper or the like. The read-out pad is held spaced from and out of contact with the permeable barrier by flange 14 or by a spacing retaining ring or the like.

The shape of the first receptacle, which functions as an incubation chamber, can be modified to accommodate needs of prototype design. Samples of the antigenic substance to be identified can be introduced into the incubation chamber from droppers, wipes, sponges, pipets, or other tools which can deliver liquid samples.

Although wide variations in the size of the test device and materials used are possible, one typical device utilizes a clear polystyrene cup about 9/16 inch outside diameter by 7/8 inch high, a polyethylene sleeve about 5/8 inch outside diameter by 3/8 inch high and a polyethylene cap about 1/4 inch by 5/8 inch.

Another exemplary form of test device is shown in FIG. 2, a modified commercial syringe-filter unit. A first receptacle 20 in the form of a cylindrical transparent or translucent syringe barrel is closed at one end and open at the other. Antigen on a solid support, such as beads 21, is introduced into the bottom of barrel 20 and liquid sample 22 is added.

A second receptacle 23 in the form of a hollow transparent or translucent plunger, open at both ends, is inserted into the open top of barrel 20. Plunger 23 engages barrel 20 for reciprocal movement therein in leak-proof sealed relation by virtue of a resilient O-ring 24 or similar annular gasket held in an annular groove or channel 25. A vent 26 is provided in the side wall of plunger 23 (or barrel 20) and is provided with a removable closure. A liquid permeable barrier 27 is positioned adjacent the lower end of plunger 23 press fit against shoulder 28.

A transparent or translucent closure cap 29 engages the open top end of plunger 23 in leak-proof sealed relation. Cap 29 has a flat top or end 30. A white porous bibulous read-out pad 31 is positioned within cap 29 end 30. If necessary a resilient washer or similar retaining ring may be used to hold barrier 27 and readout pad 31 in place.

Figure 3:
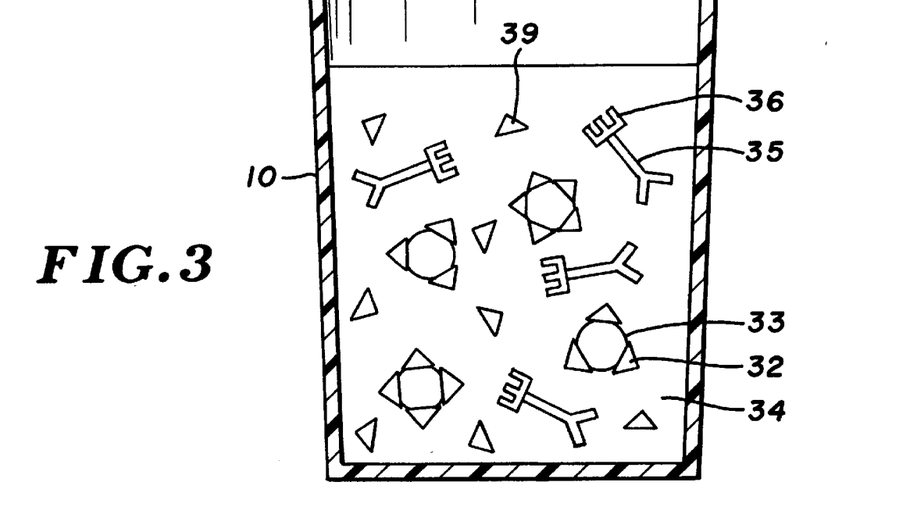
FIG. 3 is a vertical sectional view showing schematically a solution containing a mixture of known antigenic substance irreversibly attached to a solid support, a detecting agent—antibody conjugate and unknown antigenic substance to be identified, prior to incubation.
Figure 4:
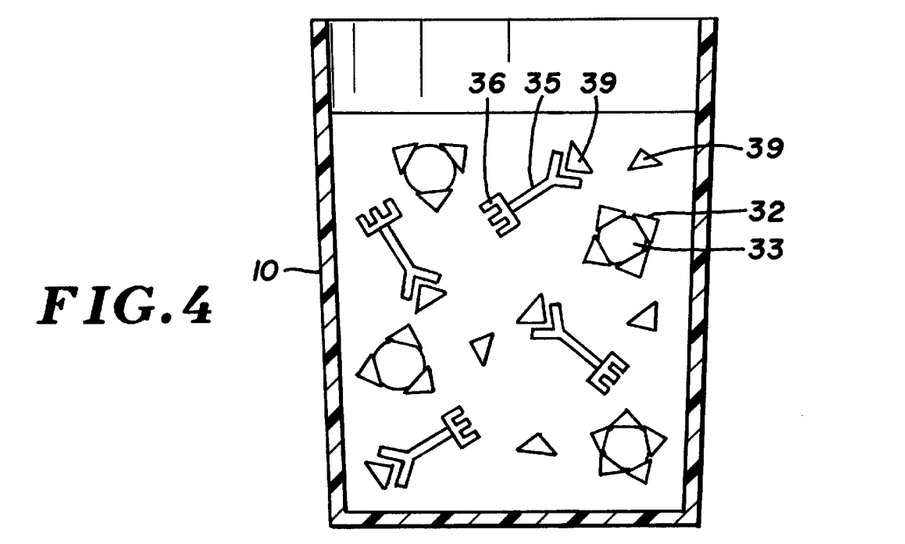
FIG. 4 is a similar sectional view showing schematically the mixture after incubation to cause the unknown antigenic substance to bind to the conjugate.
Figure 5:
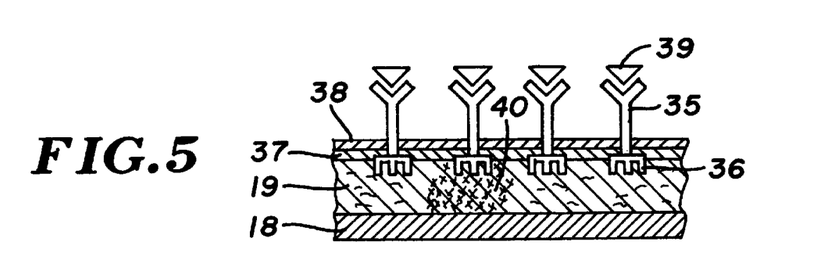
FIG. 5 is a sectional view showing schematically a color reaction between a conjugate with bound antigen, substrate for the detecting agent and a chromogen.

In carrying out the method of this invention, as shown schematically on a greatly enlarged scale in FIGS. 3 through 5, with reference to the test device of FIG. 1, a known antigenic substance 32 such as a protein, toxin, drug, microorganism, a selected moiety of a microorganism, or other entity of interest for detection purposes is irreversibly attached to a solid support 33. After adequate washing it is suspended in a buffer solution 34 of choice at a prescribed concentration and used as part of the test system.

The specific antibody 35 to the known antigenic substance is covalently coupled to a detecting agent 36, such as an enzyme like horseradish peroxidase (HRP). After purification and proper dilution, this enzyme-antibody conjugate 35–36 is used as part of the test system. The enzyme is one which reacts with a substrate to produce a color.

Besides horseradish peroxidase, some common enzymes useful in carrying out the method of this invention are alkaline phosphatase, glucoamylase, carbonic anhydrase, acetylcholinesterase, glucose oxidase, urease and beta-galactosidase. Other enzymes, such as those listed in Table III of U.S. Pat. No. 4,275,149, column 22, lines 51–69 and column 23, lines 1–48 also apply.

A variety of substrates and chromophores are available for use with these enzymes. Horseradish peroxidase, for instance, employs $H_2O_2$ and one or more of the following example chromogens to generate a colored product: 5-amino salicylic acid, 2,2'-azino-bis (3-ethyl-benzthiazoline-6-sulfamic acid), o-dianisidine, o-phenylenediamine and 3,31, 5,5'-tetramethylbenzidine. Other examples for this and other enzymes are cited in U.S. Pat. No. 4,299,916, starting in column 29 in the section entitled "Chromophores and Fluorophore Reactions". Of particular interest are the peroxidases, which require a chromogenic substrate and an acceptor such as hydrogen peroxide or uric oxide, and the hydrolases, which require only a chromogenic substrate.

A read-out sub-assembly 19 is previously prepared as follows: A white bibulous sheet material, such as porous paper, is firmly fitted into a clear or weakly translucent container, such as closure cap 17 in contact with cap end 18. A solution of chromogen in a buffer containing a polymer, such as a protein, detergent, polyglycol or polysaccharide, or a warm melted gel, such as agar or agarose, is allowed to equilibrate and is added to the porous paper. The chromogen mixture 37 on the paper is allowed to dry. Then, a solution containing a non-volatile form of enzyme substrate 38 is added directly over the dried chromogen on the paper and again allowed to dry to form a solid surface.

If the chromogen and enzyme substrate are not added together, the substrate may be introduced to the assembly by incorporating a reactive second layer in the form of another ply or lamina of paper containing the substrate for quick release to the chromogen layer. It has been found this second layer is generally not needed if proper equilibration of chromogen with polymer is performed prior to the addition of the mixture to the paper. This allows the substrate solution to be superimposed on the dried chromogen-polymer spot without creating unwanted background color. The superimposition of the reagents leads to more simplicity of device design and more convenient preparation procedures. Alternatively, the enzyme substrate may be incorporated into a reactive filter or reactive washer from which it will dissolve during the test procedure and flow to the read-out paper.

Continuing, the test procedure calls for adding a sample solution containing the antigenic substance 39 to be detected, or control solution, to a sample test device containing known antigen 32 on a solid support 33. A solution of enzyme-antibody conjugate 35–36 is added and the device closed by fitting a previously prepared read-out cap assembly on it. The device is swirled or shaken for several minutes to cause the sample antigen 39 to become bound to the conjugate 35–36. The closeable vent 11 is opened at this time and the device is inverted for a couple of minutes sufficient to fully wet the read-out pad. The vent may then be closed. The known antigen 32 is maintained out of contact with the read-out cap by barrier 15. Color 40 develops in about 15 minutes if the sample contains the antigen in question and is observed through the end 18 of the read-out cap. The read-out cap remains white if no antigen is present.

One objective of this invention is to provide a device which integrates chemical ingredients and physical design to allow the proper sequence of chemical and immunological reactions to take place, yielding a detectable color which signals the presence or absence of the substance being detected.

A second objective is to provide a device which is simple to use. No wash steps are needed, unlike most ELISA tests. No instrument, lab equipment, heating, or centrifugation is required other than the use of disposable transfer pipets. Thus, no special skills or training are required of the user.

A third objective is to provide an on-location field device having stable key reagents which reduces set-up time for the user. A fully reactive but non-volatile form of the enzyme substrate, hydrogen peroxide, is included in the test in a dry stable form. The chromogen is likewise presented in a dry stable form in the read-out cap. All of the surface-attached antigens referred to have been found to be stable and the enzyme-antibody conjugate is presented in a stable liquid form.

A fourth objective is to describe a method for enhancing the color development of the chromogen on the read-out pad. It has been found that various chromogens: o-dianisidine, 5-aminosalicylic acid, and tetramethylbenzidine, yield an enhanced color when applied to paper or other bibulous material in the presence of a water soluble polymer. Suitable polymers include proteins, peptides, polysaccharides, polyglycols, agar, and detergents. Application of the mixture is done at pH6+/−1. Full understanding of the phenomenon is not claimed, but it is thought that two factors may contribute: 1) hydrogen bonding between the oxygen and nitrogen atoms of the chromogen and oxygen and nitrogen atoms of the polymer occur and continue to occur when the chromogen is oxidized to its colored form, and 2) the polymer remains entwined in the paper or bibulous material, thus preventing the spreading of the colored chromogen.

In the absence of polymer, or when the polymer is over-diluted, the colored region is diffuse and difficult to identify. In the presence of polymer, a well-defined more deeply colored read-out region is developed.

When the polymer and chromogen are allowed to incubate for a sufficient period before applying them to the bibulous material and drying the spots, the peroxide solution may be superimposed on the same spot without obtaining background color. This increases the simplicity of the device in avoiding an extra physical layer.

A fifth objective is to provide a test device which can be sealed at the conclusion of the test, yielding an enclosed container which can be safely transported to a suitable disposal unit. This is important when toxic or objectionable materials are being handled.

The vent on the side of the vial must be opened at the time of inverting the vial to allow air displacement in the reactive porous material of the test system. After the-read-out area is fully wetted, the vent may be resealed for complete enclosure of the sample and reagents.

A sixth objective is to provide a test procedure or kit which is economical, providing an especially needed feature for groups involved in food or feed processing, medical and veterinary personnel, or others performing diagnostic screening tests for biological or chemical agents.

The biochemical and chemical materials used for preparing this test are readily available or prepared by established procedures. Plastic parts, screens and paper are available and require design forms which can be readily managed.

Details of preparation of the test materials and components are as follows:

A. Attachments of Antigen to Solid Surfaces.

Methods are well known to isolate antigens from virus particles. An antigen, however, that can be obtained from a suspension of purified virus will be almost free from contaminating host material. This is likely to provide an antigen free of other antigens. The growth of virus is frequently achieved in tissue culture, in chorioallantoic membranes or in organ tissue, such as rabbit skin. Following prescribed purification protocols, the antigens from virus particles are dissolved and stored in a soluble antigen or a nucleoprotein antigen rather than the virus particle.

The preparative methods for bacterial antigens are quite varied. Because of considerable dissimilarity of components of different bacterial species, methods of wide application are few. Bacterial antigens may be:

1) extracellular such as extracellular proteins, flagella and exopolysaccharides; 2) part of the cell wall; 3) part of the cell membrane; or 4) intracellular components.

Some parasitic antigens may be derived from animal blood infected with the parasitic organism. The blood may be cultured, as with *P. falciparium* or *B. divergens,* and parasitized erythrocytes are collected by centrifugation, washed and stored. In some cases, as with *T. brucei,* packed trypanosomes are collected free of erythrocytes. In other cases, ion exchange columns are used to purify the parasite from the infected blood. Some parasitic antigens, as with *T. gondii,* may be derived from the ascitic fluid of infected mice. Some larger parasites, as *O. gutturosa,* may be obtained by isolating adult worms from infected animals and homogenizing them. The packed parasitic organisms obtained from any of the above sources may be suspended in buffer, subjected to one or more freeze-thaw cycles and sonically disrupted. The material may then be centrifuged (e.g. 30 minutes at 10,000 rpm) to sediment the debris. Supernatant material may be further purified or may be frozen and stored for future use as stock antigen.

Antigens of microbiological nature may be purchased from such companies as Immuno-Mycologics, Inc., Biodesign International and Cambridge Medical Technology Corporation. Lipopolysaccharides, which are cell wall components, may be purchased from Sigma Chemical Company. Other antigens, such toxins of the Lectin family, can also be purchased from Sigma. Numerous commercial sources exist for other common biological antigenic substances such as proteins, lipids and polysaccharides.

Manufacturer's protocol (BioProbe International, Inc.) was used to make FMP-Sepharose-antigens.

Manufacturer's protocol (Spectrum, Inc.) was used to make SpectraCryl 1- and SpectraCryl 150-antigens.

B. Preparation of Enzyme-Antibody Conjugates.

The enzyme can be any one of a number which react with a substrate to produce a colored component. For example, peroxidase such as that obtained from horseradish, produces a blue or purple color when reacted with tetramethylbenzidine and hydrogen peroxide, or p-phenylene and hydrogen peroxide. A reddish color results with o-dianisidine and hydrogen peroxide and a yellow-orange color with 5-aminosalicylic acid. Other materials, like uric oxide, nickel peroxide, cumene hydroperoxide, and urea hydrogen peroxide addition compound, may be used to replace hydrogen peroxide as the oxygen donor. Alkaline phosphatase produces a yellow color when reacted with dintrophenylphosphate. Beta galactosidase reacts with o-nitrophenyl-beta-D-galactopyranoside to give a purple color.

Clear procedures are described in "Antibodies: A Laboratory Manual", Ed. Ed Harlow and David Lane.

C. Preparation of Read-out Pad.

One objective is to make a device which yields easy to read test results. Since it is preferred to have a colored area surrounded by a white background, a small volume (5 to 40 microliters) of the chromogen formulation must be added to the read-out paper. A concise small area in the paper is thus preferred for easy interpretation of results. For the typical device described, a colored region of about ¼ diameter is desirable. A different sized device may accommodate a different size of colored region.

At least two ways of preparing read-out pads are available. The chromogen and enzyme substrate may both be added to the read-out pad or just the chromogen may be added to the read-out pad while the enzyme substrate, hydrogen peroxide, is added to another layer in the construction of the read-out assembly. This other layer containing enzyme substrate could be in the form of a filter pad or another vehicle which quickly releases deposits of substrate.

One procedure for preparing read-out pads with both chromogen and substrate in them is as follows: A warm solution (50° to 80° C.) of 2% melted agarose in citrate-phosphate buffer, pH 6.0, containing 0.03% tetramethylbenzidine (TMB) and 0.006% hydrogen peroxide is prepared. The hydrogen peroxide may be substituted by using 0.017% urea hydrogen peroxide addition compound. Twenty microliters of the mixture are added to the center of a $17/32$" diameter porous paper, such as S & S #410, fitted in a $9/16$ I.D. polyethylene cap. This sub-assembly is then fitted with a filter or screen-washer sub-assembly and placed in a cool dry surrounding, such as in an evacuated sealed foil pouch stored in a refrigerator.

Other formulations for preparing read-out pads with both chromogen and substrate in them include substituting either 1.5% bovine serum albumin or 5% polyethylene glycol for the 2% warm melted agarose and using 0.17% urea hydrogen peroxide addition compound as the substrate. This is applied as was done above. The moistened pads are dried by standing one hour at room temperature. A modification, sometimes preferred, involves preparing either 1.5% bovine serum albumin or 5% polyethylene glycol with the 0.03% TMB but without the peroxide. After the mixture is incubated at room temperature for an hour, twenty microliters are applied to the paper and allowed to dry. A separate addition of 10 microliters of 0.7% urea hydrogen peroxide addition compound is added to the same spot and allowed to dry. In all cases, the dried read-out sub-assemblies are fitted with screen sub-assemblies and stored in a protective environment.

Preparation of read-out pads without substrate in them include the formulations described above (2% warm agarose, 1.5% bovine serum albumin, or 5% polyethylene glycol) with 0.03% TMB in a 0.001M citrate or phosphate buffer at pH 6.0. The dried read-out sub-assemblies are fitted with filter or washer sub-assemblies and stored in a protective environment.

D. Preparation of Sample.

Meat samples are prepared by shaking 25 grams of the sample with 100 milliliters of phosphate buffer, pH 6.8+/−0.4. Large particulate matter is allowed to settle out and the bulk of the solution is passed over a small loose wad of cotton in a funnel to catch fat and remaining mid-sized particles.

Samples from culture media are diluted in phosphate buffer, pH 6.8+/−0.4.

Samples from swabs, sponges, filters, vats, pipes, or other sources are either adjusted to pH 6.8 by addition of acid or base or are diluted in phosphate buffer, pH+/−0.4.

E. Incubation of Reaction Mixture.

To a reaction vial containing 35 microliters of micro-sized antigen beads or one macro-size bead are added 0.5 ml of sample or control solution. After adding a prescribed amount of antibody-enzyme conjugate, usually from 25 to 200 microliters, the vial is gently rotated or swirled. The vial should be swirled at approximately five minute intervals, to allow the beads to react with the conjugate. After 20 minutes, the read-out cap assembly is fitted on the vial. The vent on the side of the vial is opened and the vial is inverted for about three minutes. The vial is uprighted and results are recorded at 15 minutes from the time the vial was inverted.

F. Interpretation of Results.

Evaluation of color levels may be assisted by the use of a color chart. One such chart records negative results at color levels of 0 to 1. Weakly positive samples may have levels of 2 or 3. strong positive samples have color levels of 4 or greater.

Individual users may run several known negative samples to establish their criteria for weak-color negatives.

As seen from the description above, a method for preparing stable read-out pads which yield highly defined signals in the presence of low levels of enzyme conjugate has been developed.

Other antigens which may be used for attachment to particles or solid surfaces include antigenic polysaccharides such as those listed in U.S. Pat. No. 4,275,149, column 14, lines 30–63. Viruses, bacteria, parasites, fungi and other microorganisms may be used intact, lysed or fragmented and the resulting composition, or a fractionated or extracted portion, may be used for attachment to appropriate particles. Examples of such microorganisms are tabulated in U.S. Pat. No. 4,275,149, columns 15–16, lines 1–69 and column 17, lines 1–22. Such lists may be expanded to include antigen detection for microorganisms of interest in the veterinary field. Extensive examples of microbial diseases in birds and animals are referred to in 1984 Yearbook of Agriculture: Animal Health, Livestock and Pets, U.S. Government Printing Office: 1984-451-784. Some examples by way of illustration are given in the following table:

| MICROORGANISM | HOST |
| --- | --- |
| Viruses: | |
| Feline Panleukopenia Virus | Cats |
| Avian Influenza Virus | Birds |
| Pseudorabies Virus | Swine |
| Bovine Viral Diarrhea | Cattle |
| Cytomegalovirus | Man |
| Transmissible Gastroenteritis Virum | Swine |
| Bacteria: | |
| *Salmonella dublin* | Cattle |
| *Corynebacterium pseudoturberculosis* | Cattle |
| *Mycoplasma hyopneumoniae* | Swine |
| *Treponema hyodysenteriae* | Swine |
| *Brucella canis* | Dogs |
| Parasites: | |
| *Trichinella spiralis* | Swine |
| *Dicryocaulus filaria* | Sheep |
| *Dicryocaulus viviparous* | Cattle |
| *Dirofilia imunitis* | Dogs |

-continued

| MICROORGANISM | HOST |
|---|---|
| Fungi: | |
| Trichophyton spp. | Cattle, Horses |
| Microsporum spp. | Dogs, Cats |

The invention is further illustrated by the following examples:

EXAMPLE 1

Preparation of Surface-attached Antigens.

Two types of SpectraCryl activated oxirane acrylic beads were purchased from Spectrum, Incorporated. SpectraCryl 1 beads (SC-1) have a diameter range of 0.6 to 1.4 microns. SpectraCryl 150 beads (SC-150) have a diameter range of 140 to 180 microns.

Following the manufacturer's directions, the beads were washed and reacted with the following proteins in the prescribed buffers:

1 ml settled SC-1+3.6 BG spore analyte/5.6 ml 0.1M $KHPO_4$, pH 7.5

1 ml settled SC-1+7 mg Ricin/4.9 ml 0.1M $KHPO_4$, pH 7.5

0.6 ml settled SC-150+3.6 mg Ricin/4.0 ml 1.0M $KHPO_4$, pH 7.5

After 24 hours, the suspensions were centrifuged, the supernatants removed, and the pellets were washed with 0.1M $KHPO_4$. The centrifugation and washing was repeated three times. The particles were then treated with 5 ml of 10% ethanolamine in water, adjusted to pH 8.0, allowed to react for 24 hours, and again thoroughly washed with buffer. The products were stored at 4° C. until needed.

BG spore analyte and ricin were coupled to 2-fluoro-1-methylpyridinium toluene-4-sulfonate (FMP) activated Sepharose CL-4B particles, purchased from Bio-Probe, Inc., having a diameter range of 40 to 150 microns.

Following manufacturer's instructions, 3.6 mg BG analyte in 5.6 ml 0.01M borate buffered saline (BBS) at pH 8.2 was reacted with one milliliter of settled particles of FMP-Sepharose. Likewise, 7 mg ricin in 4.9 ml 0.01M BBS was reacted with 2 ml of FMP-Sepharose. After 24 hours on a rotator, the vials were centrifuged and the supernatants removed. The beads were washed three times with 7 ml Tris buffer, pH 8.0. The FMP-particles were treated with 5 ml of 0.1M phosphate buffer, pH 6.8, the products were stored at 40° C. until needed.

EXAMPLE 2

Preparation of some Enzyme-Antibody Conjugates.

Horseradish peroxidase (HRP) was coupled to affinity purified preparations of the following antibodies:

*E coli* 0157-H7, BG spore analyte, ricin, O-specific Listeria monocytogenes, H- specific *L. monocytogenes*, and BVD, using the Periodate Procedure described in "Antibodies: A Laboratory Manual" Ed. Ed Harlow and David Lane.

Affinity purified antibody to *E. coli* was also coupled to HRP using the Glutaraldehyde Method described in the same manual.

EXAMPLE 3

Preparation and Assembly of Read-out and Screen Units.

Nitrex nylon screen, product 3-40/26 from Tetko, Inc., was pre-punched at ½" diameters. To make one unit, the screen was placed in a polyethylene cap or sleeve 13 with a ⅜" hole as seen in FIG. 1. A 17/32" O.D., ¼" I.D. paper washer, made with S & S # 410 paper, is tightly pressed over the screen.

To a 17/32" diameter porous paper disk 18, S & S # 410, fitted in a 9/16" polyethylene cap 17, as seen in FIG. 1, is added 20 microliters of 0.03% tetramethylbenzidine (TMB) and 1.5% bovine serum albumin in 0.001M citrate, pH 6.0. The moist disks are allowed to dry by standing one hour at room temperature. Ten microliters of 1.5% urea hydrogen peroxide addition compound in 0.01 phosphate buffer, pH 6.8, are overlayed on the TMB and the disk is again allowed to dry for one hour.

The dried units are assembled as shown in FIG. 1, placed in a foil pouch, evacuated, sealed, and stored until needed.

Reaction vials 10 with vents, pretreated by soaking in a 1% protein solution, are dried and stored until needed.

EXAMPLE 4

Application of System for the Detection of Listeria Monocytongenes.

Purified O and H antigens were used to prepare FMP-antigen particles. Such particles were used for isolating affinity purified antibodies with specificity to either O or H antigen.

Purified antibody was conjugated to HRP and was stored frozen in the presence of 1.5% protective protein.

Stock solutions of both O and H antigens in phosphate buffer were used as references for positive samples. To individual reaction vials containing 35 microliters of antigen particles, 0.5 ml of buffer or reference solution or sample was added, followed by 50 microliters of HRP-antibody conjugate. The vials were swirled at five minute intervals. After 20 minutes, read-out caps were fitted on the vials and the vials were inverted. After about three minutes the vials were uprighted and color was recorded at 15 minutes after inverting.

Positive responses were found with reference solutions having protein concentrations from 20 nanograms/ml to 20 micrograms/ml.

EXAMPLE 5

Application of System for the Detection of BG Spore Analyte

A mouse monoclonal antibody was used for preparing a HRP-antibody conjugate. It was found a better detection system resulted when a "displacement" reaction was used rather than the more common "competitive" reaction between the antigen (BG analyte) and the antigen beads for binding sites on the enzyme-antibody conjugate.

This "displacement" reaction necessitates the preassay preparation of enzyme-antibody conjugate bound to antigen particles. An excess of conjugate is first reacted with the antigen particles. Unbound conjugate is removed by treating the mixture with a buffer containing Tween-20, centrifuging the mixture, siphoning away the supernatant, and repeating the Tween-20/centrifugal/siphoning three times. The washed conjugate antigen-particles are brought to a specified volume and used as part of the test.

Samples or controls in a 0.5 ml volume are added to test vials containing 50 microliters of a conjugateantigen-particles suspension. After placing read-out caps on the vials, the vials are gently swirled for five minutes at room temperature, then inverted for three minutes. After uprighting the vials, color is recorded after 15 minutes from the time the vials were inverted.

EXAMPLE 6

Application of System for the Detection of Ricin

The glycoprotein ricin, toxin RCA-60, was coupled to three different types of particles: FMP-Sepharose, SpectraCryl-1 (SC-1), and SpectraCryl-150 (SC-150). The later two are commercially purchased activated oxirane acrylic beads. FMP-Sepharose particles have a diameter range of 40–150 microns, SC-1 has a range of 0.6 to 1.4 microns and SC-150 has a range of 140 to 180 microns.

Screens were replaced by 17/32" paper pads in the read-out caps. The chromogen and enzyme substrate, hydrogen peroxide or other suitable peroxide, were included.

Samples or controls in a 0.5 ml volume were added to reaction vials containing 35 microliters of ricinparticles. After addition of 50 microliters of an appropriately diluted HRP-antibody conjugate, read-out caps were fitted on the vials. The vials were gently swirled at five minute intervals for 20 minutes, then inverted for three minutes. Color was recorded 15 minutes from the time the tubes were inverted.

Equivalent results were obtained by all three types of particles. A slight preference for a "competitive" reaction over a "displacement" reaction was realized.

EXAMPLE 7

Use of Syringeless Filter Apparatus

The same reagents used in Example 4 were used with a different type of device as shown in FIG. 2. The filter units of syringeless filter devices purchased from Whatman, Inc. were dissembled. The filter pads were removed and replaced by ¼" nylon screens, type 3-40/26 discussed in Example 3. Two milliliters of sample were added to the test tube portion already containing 140 microliters FMP-Sepharose particles having Listeria monosytogenes 4B antigen attached. A suitable dilution of HRP-antibody conjugate in 120 microliters of phosphate buffer was added and the tube contents were allowed to incubate for 20 minutes at room temperature with occasional swirling.

Read-out caps made earlier were stored in evacuated foil pouches. At the time of running the test, they were fitted into the plunger units and the latter fitted into the test tube, leaving the vent open.

When the incubation of conjugate, sample and particles was complete, the assembly was inverted to wet the read-out pad. After uprighting the assembly, the plunger was pushed down to cover the vent.

Positive results were recorded after 15 minutes. Positive responses were found with reference solutions having antigen concentrations from 20 nanograms/ml to 2 micrograms/ml, or roughly $10^6$ to $10^8$ cells/ml.

It is apparent that many modifications and variations of this invention as hereinbefore set forth may be made without departing from the spirit and scope thereof. The specific embodiments described are given by way of example only and the invention is limited only be the terms of the appended claims.

We claim:

1. A method for the on-location field detection of unidentified antigenic substances which are detrimental to human or animal health or welfare, which method comprises:
   A) irreversibly attaching a known antigenic substance, the detection of which is of interest, to a solid support and suspending in a buffer solution,
   B) coupling a specific antibody to said known antigenic substance to a detecting agent to prepare a conjugate comprised of said specific antibody and said detecting agent in solution,
   C) admixing a sample solution containing the suspected unidentified antigenic substance to be detected, said suspended known antigenic substance on the solid support, and said conjugate,
   D) incubating the mixture to bind the unidentified antigenic substance to said conjugate,
   E) contacting a white porous bibulous sheet material incorporating a chromogen and a substrate for said detecting agent with said conjugate with bound unidentified antigen, while maintaining said known antigen and support out of contact with said bibulous material, and
   F) observing a color reaction in said bibulous material if the unidentified antigenic substance in said sample solution is the same as that on the solid support.

2. A method according to claim 1 wherein said sample solution is first admixed with the known antigenic substance, and the conjugate in solution is then added.

3. A method according to claim 1 wherein the mixture is incubated by gentle swirling at about 5 minute intervals for about 20 minutes.

4. A method according to claim 1 wherein said solid support is composed of micro synthetic resinous plastic beads.

5. A method according to claim 4 wherein said beads are oxirane acrylic beads.

6. A method according to claim 1 wherein said detecting agent is an enzyme and said substrate is an enzyme substrate.

7. A method according to claim 1 wherein said substrate is incorporated into said sheet material from a reactive layer on the surface of the sheet material.

8. A method according to claim 1 wherein said substrate is incorporated into said sheet material by washing from a barrier maintaining the known antigen and support separate from the bibulous material.

9. A method according to claim 1 wherein said detecting agent-antibody conjugate is bound to said known antigenic substance on the solid support prior to introduction of said sample solution of unidentified antigenic substance.

10. A test device for the on-location field detection of unidentified antigenic substances which are detrimental to human or animal health or welfare, which device comprises:
   A) a first walled receptacle composed of inert transparent or translucent material and having a closed end and an open end,
   B) a second walled receptacle engageable in leak-proof sealed relation with the open end of said first receptacle and having first and second open ends,
   C) a transverse liquid permeable barrier supported within said second receptacle,
   D) a transparent or translucent closure cap engageable in leak-proof sealed relation with the second open end of said second receptacle, E) a white porous bibulous readout pad in engagement with the inside surface of said cap, said pad being spaced from said permeable barrier, F) a chromogen incorporated into said pad, and G) a substrate for a color-reactive detecting agent within the test device available for reaction with said chromogen and test material formed during use of the device.

11. A test device according to claim 10 wherein a closeable vent is provided in the wall of at least one of said receptacles.

12. A test device according to claim 10 wherein said first receptacle is a cylindrical vial and said closeable vent is in the cylindrical side wall of said vial.

13. A test device according to claim 10 wherein said second receptacle is a cylindrical collar.

14. A test device according to claim 10 wherein said permeable barrier supported within said collar is a screen or filter.

15. A test device according to claim 14 wherein said permeable barrier is an absorbent filter and said substrate is incorporated into said barrier.

16. A test device according to claim 10 wherein said substrate is incorporated into said read-out pad as a separate reactive layer on the surface of the pad.

17. A test device according to claim 10 wherein

A) said first receptacle is a cylindrical vial,

B) said second receptacle is a tubular cylindrical plunger open at each end and receivable for reciprocal movement within said first receptacle, C) said permeable barrier is supported in the open end of said plunger which is within said first receptacle, and D) said closeable vent is in the cylindrical wall of said plunger.

18. A test device according to claim 17 wherein the outer cylindrical wall of said plunger is fitted with a resilient O-ring to maintain a leak-proof sealed engagement between said plunger and vial.

19. A test device according to claim 17 wherein said permeable barrier supported within said plunger is a screen or filter.

20. A test device according to claim 19 wherein said permeable barrier is an absorbent filter and said substrate is incorporated into said barrier.

21. A method for the on-location field detection of unidentified antigenic substances which are detrimental to human or animal health or welfare, said method employing a test device comprising:

A) a first receptacle composed of inert transparent or translucent material and having a closed end and an open end, B) a second receptacle engageable in leak-proof sealed relation with the open end of said first receptacle and having first and second open ends, C) a transverse liquid permeable barrier supported within said second receptacle, D) a transparent or translucent closure cap engageable in leak-proof sealed relation with the second open end of said second receptacle, E) a white porous bibulous sheet material readout pad in engagement with the inside surface of said cap, said pad being spaced from said permeable barrier, F) a chromogen incorporated into said pad, and G) a substrate for a color-reactive detecting agent within the test device available for reaction with said chromogen and test material formed during use of the device, said method comprising:

1) irreversibly attaching a known antigenic substance, the detection of which is of interest, to a solid support and suspending in a buffer solution, 2) coupling a specific antibody to said known antigenic substance to a detecting agent to prepare a detecting agent—antibody conjugate, 3) admixing a sample solution containing the suspected unidentified antigenic substance to be detected, said suspended known antigenic substance on the solid support, and said conjugate, in the first receptacle of said test device, 4) assembling said first and second receptacles, 5) incubating the mixture to bind the unidentified antigenic substance to said conjugate, 6) inverting said test device and permitting the resulting conjugate with bound unidentified antigenic substance to pass through said permeable barrier while maintaining said known antigen and support separate from said bibulous pad in the cap, 7) contacting said white porous readout pad in said cap, said pad incorporating a chromogen, and a substrate for said detecting agent, with said conjugate with bound unidentified antigenic substance, 8) again inverting said test device and observing through the closure cap a color reaction in the readout pad if the unidentified antigenic substance in said sample solution is the same as that on the solid support.

22. A test device for the on-location field detection of unidentified antigenic substances which are detrimental to human or animal health or welfare, which device comprises:

A) a first receptacle composed of inert transparent or translucent material and having a closed end and an open end, and capable of receiving a solution containing a known antigenic substance, the detection of which is of interest, irreversibly attached to a solid support and suspended in a buffer solution, along with a specific antibody to said known antigenic substance coupled to a detecting agent in a detecting agent-antibody conjugate, and a suspected antigenic substance to be detected, which, when incubated, binds the unidentified antigenic substance to the conjugate, B) a second receptacle engageable in leak-proof sealed relation with the open end of said first receptacle and having first and second open ends, C) a transverse liquid permeable barrier supported within said second receptacle, said barrier being impermeable to said known antigen and support, while permitting passage of said conjugate with bound unidentified antigenic substance when the device is inverted, D) a transparent or translucent closure cap engageable in leak-proof sealed relation with the second open end of said second receptacle, E) a white porous bibulous readout pad in engagement with the inside surface of cap, said pad being spaced from said permeable barrier, F) a chromogen incorporated into said pad, and G) a substrate for a color-reactive detecting agent with in the test device available for observable color reaction with said chromogen and the conjugate with bound antigenic substance formed during use of the device, when the test device is inverted, if the unidentified antigenic substance in said sample solution is the same as that on the solid support.

* * * * *

UNITED STATES PATENT AND TRADEMARK OFFICE
CERTIFICATE OF CORRECTION

PATENT NO. : 5,846,745
DATED : December 8, 1998
INVENTOR(S) : DALE A. CHRISTENSEN, et al It is certified that error appears in the above-identified patent and that said Letters Patent is hereby corrected as shown below:

```
Column 3,  line 6,  "12" should be ---13---
Column 3,  line 10, "12" should be ---13---
Column 7,  line 10, ---"--- should be inserted after "1/4"
Column 7,  line 23, "50" should be ---50°---
Column 7,  line 29, ---"--- should be inserted after "9/16"
Column 8,  line 21 "strong" should be ---Strong---
Column 11, line 2, "conjugateantigen-particles" should be
            ---conjugate-antigen-particles---
```

Signed and Sealed this

Twenty-first Day of September, 1999

Attest:

Q. TODD DICKINSON

*Attesting Officer*    Acting Commissioner of Patents and Trademarks

UNITED STATES PATENT AND TRADEMARK OFFICE
CERTIFICATE OF CORRECTION

PATENT NO. : 5,846,745

DATED : December 8, 1998

INVENTOR(S) : Dale A. Christensen, et al.

It is certified that error appears in the above-identified patent and that said Letters Patent is hereby corrected as shown below:

Column 1, line 7, after "is" delete "a continuation-in-part" and insert --related to--.

Signed and Sealed this

Twenty-ninth Day of August, 2000

Attest:

Q. TODD DICKINSON

*Attesting Officer*  *Director of Patents and Trademarks*